United States Patent
Danhier et al.

(10) Patent No.: US 11,053,194 B2
(45) Date of Patent: Jul. 6, 2021

(54) PRODUCTION PROCESS FOR MAGNESIUM N-ACETYL TAURINATE

(71) Applicant: Synapharm Industrial Synthesis, Alleur (BE)

(72) Inventors: Philippe Danhier, Audregnies (BE); Pascale Azzam, Alleur (BE)

(73) Assignee: SYNAPHARM INDUSTRIAL SYNTHESIS, Alleur (BE)

( * ) Notice: Subject to any disclaimer, the term of this patent is extended or adjusted under 35 U.S.C. 154(b) by 0 days.

(21) Appl. No.: 16/896,515

(22) Filed: Jun. 9, 2020

(65) Prior Publication Data

US 2020/0392078 A1    Dec. 17, 2020

(51) Int. Cl.
| | | |
|---|---|---|
| *C07C 315/06* | (2006.01) | |
| *C07C 317/04* | (2006.01) | |
| *C07F 3/02* | (2006.01) | |
| *C07C 309/15* | (2006.01) | |

(52) U.S. Cl.
CPC .......... *C07C 315/06* (2013.01); *C07C 309/15* (2013.01); *C07C 317/04* (2013.01); *C07F 3/02* (2013.01)

(58) Field of Classification Search
CPC ... C07C 315/06; C07C 317/04; C07C 309/15; C07F 3/02
See application file for complete search history.

(56) References Cited

U.S. PATENT DOCUMENTS

| | | | | |
|---|---|---|---|---|
| 4,199,601 A | * | 4/1980 | Durlach | A61K 31/185 514/578 |
| 5,582,839 A | * | 12/1996 | McCarty | A61K 31/185 424/489 |
| 9,029,419 B2 | * | 5/2015 | Durlach | A61P 27/02 514/578 |

FOREIGN PATENT DOCUMENTS

| | | | | | |
|---|---|---|---|---|---|
| BE | 1026496 B1 | * | 2/2020 | .......... | A61K 31/131 |
| WO | WO 201907256 | * | 4/2019 | .......... | A61K 31/185 |

OTHER PUBLICATIONS

Durlach, J. et al., Mg acetyltaurinate as a photic inhibitor in photosensitive magnesium depletion: a physiological pathway in headache with photophobia treatment, Corpus ID: 35787046, 21 pages (Year: 2013).*

Arfuzir, N.N.N. et al., Protective effect of magnesium acetyltaurate against endothelin-induced retinal and optic nerve injury, Neuroscience, vol. 325, pp. 153-164 (Year: 2016).*

* cited by examiner

*Primary Examiner* — Yate' K Cutliff
(74) *Attorney, Agent, or Firm* — Hanley, Flight and Zimmerman, LLC

(57) ABSTRACT

The present invention concerns a process for the production of magnesium N-acetyl taurinate, in particular a process for the production of magnesium N-acetyltaurinate dihydrate.

20 Claims, No Drawings

PRODUCTION PROCESS FOR MAGNESIUM N-ACETYL TAURINATE

This patent arises claims priority to Belgian Patent Application BE 2019/5372, which was filed on Jun. 11, 2019, and which is hereby incorporated by reference in its entirety for all purposes.

The present invention concerns a process for the production of magnesium N-acetyl taurinate, in particular a process for the production of magnesium N-acetyl taurinate dihydrate.

N-acetyl-taurine salts are essentially obtained by means of a process similar to that used to prepare sodium acetyl taurinate as described by Teracoka (Teracoka, *Hoppe-Seyler's Zeitschrift für Physiologische Chemie*, 145, 1925, 242), i.e. by reacting acetic anhydride with taurine in the presence of a base corresponding to the desired salt at the mixture's boiling point. Magnesium N-acetyl taurinate is generated by the acetylation of taurine (a sulphonated amino acid) in the presence of a magnesium compound, e.g. magnesium hydroxide or oxide. Acetylation occurs at the taurine's nitrogen atom (a $NH_2$ group), thereby abolishing the molecule's zwitterionic character with only the negative charge of the sulphonate group ($SO_3H$) remaining. This makes magnesium N-acetyl taurinate more lipophilic which notably facilitates its passage across the neuronal phospholipid membrane. N-acetyl-taurine affords access to novel taurine properties, in particular by enhancing its ability to enter cells which amplifies the neuromuscular activities of 2-aminoethanesulphonic acid. In particular, acetylation enhances the ability of many organic sulphur-containing compounds to enter cells without compromising their biological activities.

Document FR2384751 describes a production process in which magnesium N-acetyl taurinate is obtained by mixing magnesia, taurine, water and acetic acid followed by two successive drying steps, one in a vacuum at 100° C. and another with a desiccating solvent, in such a way as to ensure slow crystallisation in the course of cooling to room temperature. The yield of this production process with respect to the amount of magnesia input is of the order of 65% ([weight of magnesia input/weight of magnesium N-acetyl taurinate obtained at the end of the production process]*100).

In addition to the production process for magnesium N-acetyl taurinate described in Document FR2384751, the article by Arfuzir (Arfuzir et al., Protective effect of magnesium acetyltaurinate against endothelin-induced retinal and optic nerve injury, *Neuroscience* 325, 2016, 153-164) describes a different production process for magnesium N-acetyl taurinate. This process involves the following steps: (a) addition of taurine and magnesium oxide to water; (b) mixing of the solution obtained in step (a) at a temperature of 80-90° C. for 10 minutes with the addition of acetic anhydride; (c) mixing of the solution obtained in step (b) at a temperature of 80-90° C. for 30 minutes; (d) vacuum evaporation of the solution obtained in step (c); (e) treatment of the residue obtained by evaporation in step (d) with ethanol (ethyl alcohol) and then cooling in a refrigerator for 24 hours to generate a precipitate; (f) filtration of the precipitate obtained in step (e) and successive cold washes with ethanol (ethyl alcohol), acetone and diethyl ether; (g) air-drying at room temperature of the washed precipitate obtained in step (f) then vacuum-drying at 40-50° C. to yield the final anhydrous magnesium N-acetyl taurinate (formula $C_8H_{16}MgN_2O_8S_2$, molecular weight 356.656) in powder form. The yield of this process with respect to the magnesium input is of the order of 90% ([weight of magnesium oxide input/weight of magnesium N-acetyl taurinate obtained at the end of the production process]*100).

Magnesium N-acetyl taurinate ($C_8H_{16}MgN_2O_8S_2$) is notably known for its cytovascular protective properties such as antiplatelet activity, an ability to protect against venous and arterial thrombosis, and stabilising activity vis-a-vis the erythrocyte membrane. In addition, magnesium N-acetyl-taurinate has been shown to protect against glaucoma by acting on vascular deregulation, and to have angioprotective properties by virtue of anti-inflammatory activity based on restoring levels of endothelial Nitric Oxide Synthase 3 (eNOS-3). Studies have also shown magnesium N-acetyl-taurinate to have beneficial effects on neurotoxicity associated with hyperexcitable glutamatergic ion-channel receptors. In fact, magnesium N-acetyl-taurinate acts within neurones not only at the NMDA receptor but also on two other glutamate-gated ion-channels, namely the AMPA and KA, both involved in the speed of synaptic transmission. It has been noted that such a compound shows structural analogy with both glutamic acid and kainic acid so magnesium N-acetyl taurinate would target all the glutamatergic receptors—NMDAR, AMPAR and KAR—to inhibit signalling pathways downstream of all of them.

Unfortunately, although magnesium N-acetyl taurinate has many useful properties, the production process for magnesium N-acetyl taurinate described in Document FR2384751 only gives a yield of the order of 65% with respect to the amount of magnesium input. Furthermore, the process of Arfuzir et al. requires successive washes with ethanol (ethyl alcohol), acetone and diethyl ether, organic substances that generate environmentally damaging toxic waste and are hazardous for the technician carrying out the magnesium N-acetyl taurinate synthesis. Moreover, although the production process for magnesium N-acetyl taurinate described in Arfuzir et al. gives a yield of the order of 90% with respect to the amount of magnesium input, it nevertheless requires a long cooling step lasting at least 24 hours as well as high-temperature (>50° C.) heating steps. The Arfuzir et al. process therefore consumes a great deal of energy to provide major cooling as well as heating to high temperatures. This affects the global yield of this process.

There is therefore a need for a viable process for the production of magnesium N-acetyl taurinate that reduces organic inputs, is more environmentally friendly (reducing toxic waste and energy consumption), makes it possible to obtain magnesium N-acetyl taurinate more quickly, cuts down the exposure of technicians to hazardous, toxic substances and affords yields that are at least equivalent—or greater than—those achieved with existing processes.

To address at least some of these issues, the invention provides a process for the production of magnesium N-acetyl taurinate, in particular a process for the production of magnesium N-acetyl taurinate dihydrate, consisting of:

a) a dissolution step (i) of taurine, (ii) of at least one magnesium compound, e.g. magnesium oxide or magnesium hydroxide and (iii) acetic anhydride in water with salt formation and acetylation of the said taurine to generate a solution containing acetylated magnesium taurinate;

b) a step of evaporation and/or distillation of said solution obtained in step a) to remove at least some of the excess water and acetic acid and generate a first precipitate, in particular a first precipitate in distillate form, containing the acetylated magnesium taurinate;

c) at least one water washing step, e.g. by filtration, of said first precipitate obtained in step b), said water washing step being followed by a step d) of evaporation and/or distillation to remove at least some of the excess water and acetic acid and generate a second precipitate, in particular a second precipitate in distillate form, containing the acetylated magnesium taurinate;

d) at least one wash step, with a rinse solution containing ethanol, preferably a rinse solution containing only ethanol, of said second precipitate obtained in step d), said wash step with a rinse solution containing ethanol, preferably a rinse solution containing only ethanol, being followed by a step f) of evaporation and/or distillation to remove at least some of the excess water and ethanol and generate a third precipitate containing the acetylated magnesium taurinate;

g) a cooling step of said third precipitate obtained in step f);

h) a step of purification and/or washing of said cooled-down third precipitate obtained in step g) to generate a fourth precipitate in cake form; and i) a drying/desiccation step of said purified and/or washed fourth precipitate in cake form obtained in step h).

The process according to the present invention uses only ethanol or water for the washing steps which considerably cuts down organic inputs and therefore the amount of environmentally damaging toxic waste that is generated. Moreover, the ethanol used can be re-used for other washing steps when the process is run again. Finally, the process according to the present invention affords a yield of the order of 92% with respect to the amount of magnesium input and does not require a cooling step lasting at least 24 hours: the process according to the invention therefore gives a better yield than processes in the background art and significantly cuts down the amount of energy needed to generate magnesium N-acetyl taurinate.

Advantageously, according to the invention, the magnesium N-acetyl taurinate obtained is magnesium N-acetyl taurinate dihydrate including two intrinsic water molecules. In the sense of the present invention, the term "two intrinsic water molecules" means that the two water molecules constitute an integral part of the magnesium N-acetyl taurinate dihydrate molecule as opposed to any water of hydration which could be absorbed or adsorbed by this compound. The magnesium N-acetyl taurinate dihydrate ($C_8H_{20}MgN_2O_{10}S_2$), also called Magnesium N-Acetyltaurinate dihydrate, is a magnesium vector and a magnesium analogue of taurine with a molecular weight of 392.677 g/mol, two molecules of water ($H_2O$) being intrinsic to the magnesium N-acetyl taurinate dihydrate molecule. The molecular weight of magnesium N-acetyl taurinate dihydrate differs from that of unhydrated magnesium N-acetyl taurinate ($C_8H_{11}MgN_2O_8S_2$) which is 356.656 g/mol.

Like unhydrated magnesium N-acetyl taurinate, magnesium N-acetyl taurinate dihydrate containing two intrinsic water molecules possesses various characteristics such as a sulphated amine β-derivative, a sulphonic (non-carboxylic) acid, a N-acetylate, and does not present the amphoteric character of taurine (a zwitterion with a positive and a negative charge present on the same group) which optimises intracellular taurinergic activity. Since the electrical charge on the nitrogen of the taurine has been abolished by acetylation, only the electrons of the Mg++ cation are kept chelated by the taurine's two sulphonic groups. This yields an ethanamide (acetamide) derivative which is more lipophilic than amphoteric taurine. This promotes entry across the neuronal phospholipid membrane. Ethanamide (acetamide) derivatives characterise compounds used for their nootropic (like piracetam), anticonvulsive and anti-epileptic (like levitracitam) activities.

According to one embodiment of the invention, said step a) of dissolution in water is achieved by the addition—simultaneously or staggered in time—of said taurine, said magnesium compound (e.g. magnesium oxide or magnesium hydroxide) and said acetic anhydride. For example, the taurine and the magnesium compound could be dissolved in water first to generate a first solution before addition of the acetic anhydride later (e.g. added progressively by exothermic flow) to generate a second solution which then contains acetylated magnesium taurinate.

Preferably, according to the production process for magnesium N-acetyl taurinate addressed in this invention, step h) of purification and/or washing of said third precipitate is achieved by filtration in the presence of a filtration solution, preferably in the presence of a filtration solution containing ethanol.

Advantageously, in the production process for magnesium N-acetyl-taurinate according to the invention, step h) of purification and/or washing of said third precipitate is achieved by centrifugation in the presence of a centrifugation solution, preferably in the presence of a centrifugation solution containing ethanol.

Preferably, in the production process for magnesium N-acetyl-taurinate according to the invention, step h) of purification and/or washing of said third precipitate by centrifugation is carried out at a spin speed of between 500 and 1500 revolutions per minute, preferably at a spin speed of between 800 and 1200 revolutions per minute.

Advantageously, in the production process for magnesium N-acetyl-taurinate according to the invention, step a) of dissolution is carried out in the presence of a dissolution solution containing ethanol.

Preferably, in the production process for magnesium N-acetyl-taurinate according to the invention, step a) and/or step b) and/or step d) and/or step f) and/or step h) and/or step i) is carried out in a vacuum. In particular, in the framework of the present invention, it has been determined that when step a) and/or step b) and/or step d) and/or step f) and/or step h) and/or step i) is carried out in a vacuum, the yield of the process with respect to the amount of magnesium input is enhanced. According to the invention, nitrogen or any other inert gas can be used to generate the vacuum. Similarly, any method that can be used to generate a vacuum may be exploited in the framework of the present invention. In particular, when any of steps a), b), d), f), h) or i) is carried out in a vacuum, the kinetics of the acetylation reaction in the process according to the invention are markedly shifted in favour of acetylation by displacement of the chemical equilibrium, in line with the Le Chatelier principle.

Preferably, according to the production process for magnesium N-acetyl taurinate according to the invention, step a) and/or step b) and/or step c) and/or step d) and/or step e) and/or step f) and/or step g) and/or step h) and/or step i) is carried out at a temperature of 50° C. or below. In particular, in the framework of the present invention, it has been determined that when step a) and/or step b) and/or step c) and/or step d) and/or step e) and/or step f) and/or step g) and/or step h) and/or step i) is carried out at a temperature of 50° C. or below, the yield of the process is enhanced with respect to the amount of magnesium input. In particular, when at least one of steps a), b), c), d), e), f), g), h) or i) is carried out at a temperature of 50° C. or below, the kinetics of the acetylation reaction in the process according to the invention are markedly shifted in favour of acetylation by displacement of the chemical equilibrium, in line with the Le Chatelier principle.

According to one preferred embodiment of the invention, step a) of dissolution is carried out in a vacuum at a temperature of 50° C. or below. It has been shown that doing this markedly shifts the kinetics of the acetylation reaction in the process according to the invention in favour of acetylation (in line with the Le Chatelier principle) as well as optimising the rate of the reaction. More particularly, performing the dissolution in a vacuum at a temperature of 50° C. or below facilitates the extraction of gaseous acetic acid produced in excess by hydrolysis of the acetic anhydride in water, which also favours the acetylation reaction.

In another preferred embodiment according to the invention, steps a) of dissolution, h) of purification and/or washing of said cooled-down third precipitate and i) of drying/desiccation of said purified and/or washed fourth precipitate in cake form are carried out in a vacuum at a temperature of 50° C. or below. Above and beyond the facts that the kinetics of the acetylation reaction of the process according to the invention are markedly favoured by displacement of the chemical equilibrium in favour of acetylation (in line with the Le Chatelier principle) and that the reaction rate is optimised in such conditions, it has also been shown that doing this optimises the global yield of the process according to the invention.

In yet another preferred embodiment according to the invention, steps a) of dissolution, h) of purification and/or washing of said cooled-down third precipitate by centrifugation in the presence of a centrifugation solution, preferably in the presence of a centrifugation solution containing ethanol and i) of drying/desiccation of said purified and/or washed fourth precipitate in cake form are carried out in a vacuum at a temperature of 50° C. or below. Above and beyond the facts that the kinetics of the acetylation reaction of the process according to the invention are markedly favoured by displacement of the chemical equilibrium in favour of acetylation (in line with the Le Chatelier principle) and that the reaction rate is optimised in such conditions, it has also been shown that doing this further improves the global yield of the process according to the invention.

According to the invention, said drying/desiccation step of said purified and/or washed fourth precipitate in cake may be performed by filtration.

The present invention also concerns a product (directly) obtained using the process according to the invention.

Other characteristics, details and advantages of the invention will emerge in the non-limiting examples given hereafter.

COMPARATIVE EXAMPLE

The process according to the present invention has been compared to the processes respectively described in Document FR2384751 and the article of Arfuzir et al. in terms of yields with respect to the amount of magnesium input. More particularly, the process according to the invention was compared to the two processes known in the background art:
a) dissolution, in a vacuum at a temperature of 50° C., (i) of 0.2 M taurine, (ii) 0.102 M magnesium hydroxide, and (iii) 0.265 M acetic anhydride in water with salt formation and acetylation of the taurine to generate a solution containing acetylated magnesium taurinate;
b) distillation in a vacuum at a temperature of 50° C. de la solution obtained in step a) to remove at least some of the excess water and acetic acid and generate a first precipitate in the form of a distillate containing the acetylated magnesium taurinate;
c) filtration washing in water of the first precipitate obtained in step b), with a water wash step being followed by a step d):
d) of vacuum distillation at a temperature of 50° C. to remove at least some of the excess water and acetic acid and generate a second precipitate in the form of a distillate containing the acetylated magnesium taurinate;
e) washing, with a rinse solution containing only ethanol, of the second precipitate obtained in step d), with a wash step using a rinse solution containing only ethanol being followed by a step f):
f) of vacuum distillation at a temperature of 50° C. to remove at least some of the excess water and ethanol and generate a third precipitate containing the acetylated magnesium taurinate;
g) cooling down to a temperature of about 20-25° C. of the third precipitate obtained in step f);
h) purification, by vacuum centrifugation at a temperature of 50° C. with a rotation speed of 800-1200 revolutions per minute, of the cooled-down third precipitate obtained in step g) to generate a fourth precipitate in cake form; and
i) a drying/desiccation step at a temperature of 50° C. of the purified and/or washed fourth precipitate in cake form obtained in step h).

For each of these processes, yields obtained with respect to the amount of magnesium input are presented in Table 1 below. Yields were calculated as follows: [weight of the magnesium compound input/weight of the magnesium N-acetyl taurinate obtained at the end of the production process]*100.

TABLE 1

|  | Yield (%) |
| --- | --- |
| Process according to FR2384751 | 65 |
| Process according to Arfuzir et al. | 90 |
| Process according to the invention | 92 |

As can be clearly seen, the process according to the invention gives a better yield with respect to the amount of magnesium input than either of the two processes known in the background art. Moreover, in contrast to the Arfuzir process, the process according to the invention uses only water and just one organic substance (ethanol) for the washing steps rather than three different organic liquids (ethanol+acetone+diethyl ether).

The present invention has been described in terms of specific embodiments which are purely illustrative in value and should not be considered as limiting. In general terms, it will seem obvious to those skilled in the art that the present invention is not limited to the examples illustrated and/or described above.

Use of the verbs "contain", "consist of", "include" and "carry" or any variants or conjugate forms cannot in any way exclude the presence of elements other than those mentioned.

Use of the indefinite article "a" or "an", or of the definite article "the" to introduce an element does not exclude the possibility that more than one of said element can be present.

The invention claimed is:
1. A process for producing magnesium N-acetyl taurinate the process comprising:
a. dissolving (i) taurine, (ii) a magnesium compound, and (iii) acetic anhydride in water to cause formation of a salt and acetylation of the taurine to generate a solution containing acetylated magnesium taurinate;

b. at least one of evaporating or distilling said solution obtained in step a) to remove at least some excess water and acetic acid and to generate a first precipitate, the first precipitate containing the acetylated magnesium taurinate;

c. washing, with water, said first precipitate obtained in step b);

d. at least one of evaporating or distilling to remove at least some of the excess water and the acetic acid and to generate a second precipitate, the second precipitate containing the acetylated magnesium taurinate;

e. washing, with a rinse solution containing ethanol, said second precipitate obtained in step d);

f. at least one of evaporating or distilling to remove at least some of the excess water and ethanol and to generate a third precipitate containing the acetylated magnesium taurinate;

g. cooling said third precipitate obtained in step f);

h. at least one of purifying or washing said cooled-down third precipitate obtained in step g) to generate a fourth precipitate in cake form; and i. drying said fourth precipitate in cake form obtained in step h).

2. The process according to claim 1, wherein the dissolving of step a) includes adding said taurine, said magnesium compound, and said acetic anhydride.

3. The process according to claim 1, in which the at least one of purifying or washing of step h) includes filtering with a filtration solution containing ethanol.

4. The process according to claim 1, in which the at least one of purifying or washing of step h) includes centrifuging with a centrifugation solution containing ethanol.

5. The process according to claim 4, wherein the centrifuging includes rotating the third precipitate at a rotation speed of between 500 and 1500 revolutions per minute.

6. The process according to claim 1, wherein the dissolving of step a) includes using a dissolution solution containing ethanol.

7. The process according to claim 1, further including performing one or more of step a), step b), step d), step f), step h) or step i) in a vacuum.

8. The process according to claim 1, further including performing one or more of step a), step b), step c), step d), step e), step f), step g), step h), or step i) at a temperature of 50° C. or below.

9. The process according to claim 1, further including performing step a) in a vacuum and at a temperature of 50° C. or below.

10. The process taurinate according to claim 1, further including performing steps a), h), and i) in a vacuum at a temperature of 50° C. or below.

11. The process according to claim 4, further including performing steps a), h), and i) in a vacuum at a temperature of 50° C. or below.

12. The process of claim 1, wherein the magnesium compound includes magnesium oxide or magnesium hydroxide.

13. The process of claim 1, wherein the first precipitate is in distillate form.

14. The process of claim 1, wherein the washing includes filtering.

15. The process of claim 1, wherein the second precipitate is in distillate form.

16. The process of claim 1, wherein the rinse solution contains only ethanol.

17. The process of claim 1, wherein the magnesium N-acetyl taurinate is magnesium N-acetyl taurinate dihydrate.

18. The process of claim 2, wherein adding the taurine, the magnesium compound, and the acetic anhydride includes adding the taurine, the magnesium compound, and the acetic anhydride simultaneously.

19. The process of claim 2, wherein adding the taurine, the magnesium compound, and the acetic anhydride includes staggering the addition of the taurine, the magnesium compound, and the acetic anhydride over time.

20. The process of claim 5, wherein the centrifuging includes rotating the third precipitate at a rotation speed of between 800 and 1200 revolutions per minute.

* * * * *

UNITED STATES PATENT AND TRADEMARK OFFICE
CERTIFICATE OF CORRECTION

PATENT NO. : 11,053,194 B2  
APPLICATION NO. : 16/896515  
DATED : July 6, 2021  
INVENTOR(S) : Philippe Danhier and Pascale Azzam Page 1 of 1

It is certified that error appears in the above-identified patent and that said Letters Patent is hereby corrected as shown below:

On the Title Page

Item [30], insert:  
-- Foreign Application Priority Data  
June 11, 2019 (BE) ............................2019/5372 --

Signed and Sealed this  
Eighteenth Day of January, 2022

Drew Hirshfeld  
*Performing the Functions and Duties of the*  
*Under Secretary of Commerce for Intellectual Property and*  
*Director of the United States Patent and Trademark Office*